United States Patent
Fukuhara et al.

(10) Patent No.: US 8,122,951 B2
(45) Date of Patent: Feb. 28, 2012

(54) SYSTEMS AND METHODS OF DOWNHOLE THERMAL PROPERTY MEASUREMENT

(75) Inventors: Masafumi Fukuhara, Kanagawa-ken (JP); Kasumi Fujii, Tokyo (JP); Yoko Morikami, Sagamihara (JP)

(73) Assignee: Schlumberger Technology Corporation, Sugar Land, TX (US)

(*) Notice: Subject to any disclaimer, the term of this patent is extended or adjusted under 35 U.S.C. 154(b) by 83 days.

(21) Appl. No.: 11/346,926

(22) Filed: Feb. 3, 2006

(65) Prior Publication Data

US 2006/0191683 A1   Aug. 31, 2006

Related U.S. Application Data

(60) Provisional application No. 60/657,207, filed on Feb. 28, 2005.

(51) Int. Cl.
*E21B 47/00* (2006.01)

(52) U.S. Cl. .................. 166/250.01; 166/60; 166/302

(58) Field of Classification Search ............ 166/205.01, 166/250.1, 60, 61, 272.1, 288, 302
See application file for complete search history.

(56) References Cited

U.S. PATENT DOCUMENTS

| | | | |
|---|---|---|---|
| 2,311,757 A | 2/1943 | Jakosky | |
| 2,484,063 A * | 10/1949 | Ackley | 392/304 |
| 3,807,227 A | 4/1974 | Smith, Jr. | |
| 3,864,969 A | 2/1975 | Smith, Jr. | |
| 3,938,383 A | 2/1976 | Sayer | |
| 4,343,181 A * | 8/1982 | Poppendiek | 73/152.13 |
| 4,765,182 A * | 8/1988 | Boone | 73/152.04 |
| 5,247,994 A * | 9/1993 | Nenniger | 166/303 |
| 5,401,956 A | 3/1995 | Dunphy et al. | |
| 6,497,279 B1 * | 12/2002 | Williams et al. | 166/250.01 |
| 2003/0179651 A1 * | 9/2003 | Nutt et al. | 367/25 |
| 2004/0129417 A1 * | 7/2004 | Nelson et al. | 166/177.4 |
| 2004/0244970 A1 * | 12/2004 | Smith, Jr. | 166/250.01 |
| 2006/0032637 A1 | 2/2006 | Ayoub et al. | |

FOREIGN PATENT DOCUMENTS

| | | |
|---|---|---|
| JP | 2001-281071 A | 10/2001 |
| RU | 2136880 | 9/1999 |
| RU | 21412102 | 11/1999 |
| RU | 2169441 | 6/2001 |
| RU | 2171363 | 7/2001 |
| RU | 2190209 | 9/2002 |
| RU | 2194160 | 12/2002 |
| RU | 2194855 | 12/2002 |
| RU | 2231635 C1 | 6/2004 |
| SU | 363002 | 7/1972 |
| SU | 732515 | 5/1980 |
| SU | 1574796 A1 | 6/1990 |

* cited by examiner

*Primary Examiner* — Brad Harcourt
(74) *Attorney, Agent, or Firm* — Jianguang Du; Jody DeStefanis; Jeff Griffin

(57) ABSTRACT

Methods and systems of measuring in-situ time variant temperature for subsurface formations utilizing an active heating and/or cooling device and temperature sensors for purposes of characterizing hydrocarbon-bearing formations by deriving formation thermal properties.

25 Claims, 12 Drawing Sheets

SYSTEMS AND METHODS OF DOWNHOLE THERMAL PROPERTY MEASUREMENT

RELATED APPLICATION DATA

The present application claims priority under 35 U.S.C. §119 to U.S. Provisional Application Ser. No. 60/657,207, naming Masafumi Fukuhara and Kasumi Fujii as inventors, and filed 28 Feb. 2005, which is incorporated herein by reference in its entirety for all purposes.

FIELD OF THE INVENTION

The present invention relates to methods and systems of deriving thermal properties of subsurface structures by downhole dynamic thermal measurements. In particular, the present invention relates to utilizing an in situ active cooling and/or heating device to disturb local downhole temperature in formations, such as oil/gas bearing structures, water saturated formations, gas hydrate bearing rocks and sediments, and measuring thermal response data thereof for purposes of characterizing the formation.

BACKGROUND OF THE INVENTION

Some naturally occurring resources, such as gas hydrates, dissociate or form, or are otherwise affected, when temperature and/or pressure conditions cross the equilibrium border. An understanding of the parameters for such behavior is important for efficient exploration and development of the resources, for example, gas hydrates and heavy oils as energy resources. In this, thermal measurements are one of the key components in characterizing subsurface structures, not only statically but also dynamically.

Conventional methods to estimate thermal properties, such as thermal conductivity, capacity and diffusivity, of subsurface formations include monitoring temperatures passively at several underground depth locations and interpreting the collected data with assumptions such as steady heat flow or relaxation from thermal disturbance by drilling and/or mud circulation, etc. In conventional systems, temperature changes caused by a production test or drilling/circulation operations are measured. Because the thermal properties are estimated based on several assumptions, the passive measurement methods described above leave large uncertainties in the estimated thermal properties of the subsurface structures.

On the other hand, active thermal property measurements may be undertaken in a laboratory and equipment is commercially available for these purposes. However, applications of the laboratory based active measurement methods to in situ subsurface formation measurements have many technical and logistical difficulties.

SUMMARY OF THE INVENTION

In consequence of the background discussed above, and other factors that are known in the field of thermal characterization of subsurface formations, applicants discovered methods and systems for active subsurface thermal property measurements based on the principle that the thermal response time of subsurface structures would vary in zones having different thermal properties. In this, the present invention contemplates utilizing active heating and/or cooling, i.e., known temperature disturbances or stimulations caused by sending a known signal into subsurface formations, as opposed to passive monitoring for purposes of characterizing the subsurface formations.

Applicants recognized that dynamic measurement methodology disclosed herein would have particular applicability to in situ active measurements of subsurface structures, such as gas hydrate and/or heavy oil bearing formations.

Applicants further recognized that in situ characterization of thermal properties is one of the key components for characterization of subsurface formations.

Applicants also recognized that acquiring thermal properties of downhole structures, such as hydrocarbon bearing formations and sediments, would be highly beneficial in designing efficient systems and methods for treating the subsurface structures for the development and production of natural reserves.

The present invention contemplates dynamic measurements of temperature time variance, i.e., the thermal response is not static in time, to derive static thermal properties for formation analysis of, for example, rocks, sediments and such other subsurface formations with deposits, such as oil, gas, methane hydrates, water, among others contemplated by the present invention. In this, characterizing a formation may comprise providing one or more answer products based on one or more thermal properties of the formation, for example, answer products relating to one or more of characteristics of hydrocarbons in the formation for heat treatment of the hydrocarbons; one or more physical parameters of the formation for delineating the formation; permanent monitoring of an operating well traversing the formation; among others that are realizable based upon the teachings of the present invention.

Applicants discovered that an algorithmic relationship may be utilized advantageously to derive thermal properties, such as thermal conductivity, based on configuring a heater and/or cooler and one or more sensors in localized and/or distributed arrangements to acquire time variance of local temperature data for subsurface formations under investigation.

In one embodiment of the invention, a distributed temperature sensing (DTS) downhole system having a fiber sensor may be utilized as a temperature sensor with a localized cooling device, such as a Peltier device, and/or a heating device, such as a resistance heater that is configured by, for example, applying current to a metal and/or plastic or similar tube around the fiber sensor. In other embodiments of the invention, the configuration may include a localized precision thermometer, such as a resistor temperature detector (RTD) or a Fiber Bragg Grating sensor, and a suitably configured power supply to provide temperature control of the cooling and heating device.

In accordance with one aspect of the instant invention, one method of deriving one or more thermal properties of a subsurface formation for characterizing the formation comprises creating thermal disturbance downhole, acquiring thermal response data for the formation based on time variation in temperature, and deriving a thermal property of the formation based on the thermal response data of the formation. According to other aspects of the present invention, a system for deriving thermal properties of a subsurface formation comprises at least one of a heating and cooling device configured for creating thermal disturbance downhole in a predetermined area of interest and a sensing system configured for acquiring thermal response data and deriving a thermal property of the formation based on time variation in downhole temperature.

Additional advantages and novel features of the invention will be set forth in the description which follows or may be learned by those skilled in the art through reading the materials herein or practicing the invention. The advantages of the invention may be achieved through the means recited in the attached claims.

BRIEF DESCRIPTION OF THE DRAWINGS

The accompanying drawings illustrate preferred embodiments of the present invention and are a part of the specification. Together with the following description, the drawings demonstrate and explain principles of the present invention.

Figure 1:
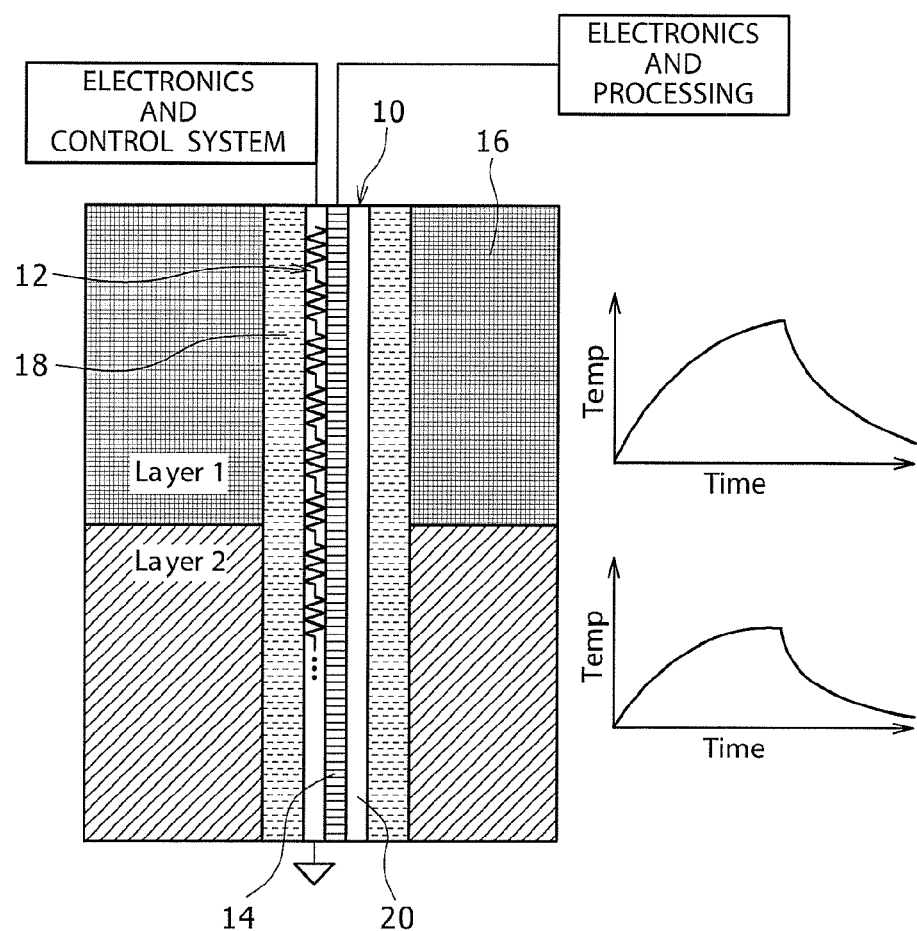
FIG. 1 is a schematic view of one exemplary context in which the present invention may be used to advantage and depicts graphically expected temperature behavior, i.e., thermal response, of layers having different thermal properties.

Throughout the drawings, identical reference numbers indicate similar, but not necessarily identical elements. While the invention is susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the scope of the invention as defined by the appended claims.

DETAILED DESCRIPTION

Illustrative embodiments and aspects of the invention are described below. In the interest of clarity, not all features of an actual implementation are described in the specification. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such development effort might be complex and time-consuming, but would nevertheless be a routine undertaking for those of ordinary skill in the art having benefit of the disclosure herein.

Stability of formation fluids, including hydrocarbons such as gas hydrates and heavy oils, is sensitive to variations in pressure (P) and temperature (T). In this, gas hydrates dissociate or form when pressure and/or temperature conditions cross the equilibrium border. As discussed above, conventional methods to acquire thermal properties of subsurface formations, such as thermal conductivity, diffusitivity, capacity, include core analysis in a laboratory and passive temperature measurements at several underground locations. For core analysis of hydrate bearing zones, for example, it is often difficult to keep the same conditions in a laboratory as the conditions that are found downhole. Data obtained are dependent upon coring conditions due to the dynamic dissociation/formation process of hydrates, compaction factor differences under different pressures, and sometimes upon missing core samples from certain depth intervals. For passive measurements at several underground locations, the acquired data are interpreted under certain assumptions that increase uncertainties, such as steady heat flow and relaxation from thermal disturbances by drilling and/or mud circulation. Furthermore, detailed thermal measurements in hydrate bearing zones have not been conducted.

The present invention contemplates utilizing thermal property measurement methods for in situ evaluation of formation thermal properties by actively creating a known thermal disturbance with a thermal source, such as a cooler and/or heater device, and monitoring the thermal response, i.e., time variant temperature data, of the target zone downhole. In this, the present invention contemplates measuring temperature of the formation area or areas in which the thermal disturbance is caused for a predetermined period of time so that the thermal response of the formation may be determined. The predetermined period of time for temperature measurements depends on surrounding conditions, such as formation properties, borehole fluids, configurations of the systems that are used, among other factors that determine a desirable or necessary period of time for the temperature measurements. Moreover, the predetermined period of time for temperature measurements may include the time period of active heating or cooling of the formation and a suitable period of time after the active heating or cooling so that sufficient thermal response data of the formation are acquired for purposes of the instant invention.

Thermal disturbance may be local heating or cooling, i.e., in a localized area of interest, so as to keep the thermal disturbance in an area or areas of the formation under investigation. The present invention contemplates actively heating or cooling the formation so as to cause dynamic thermal disturbance therein for a predetermined period of time so that the thermal response of the formation may be determined. The predetermined period or periods of time for active heating or cooling of the area/areas of interest depend on surrounding conditions, such as formation properties, borehole fluids, configurations of the systems, among other factors that determine a sufficient period of time for the heating or cooling.

Although as described herein, one embodiment of the present measurement methodology is based on a hot wire method for measuring thermal properties, other methods are within the scope of the present invention. In this, the present invention additionally contemplates systems and methods of measuring one or more thermal properties of hydrocarbon-bearing formations that do not utilize symmetrical and/or infinite length assumptions of the hot wire method.

From temperature relaxation with an infinite line heater and a temperature sensor on the heater in an infinite medium, thermal properties are derived for the surrounding medium. The relationship of thermal conductivity and temperature is shown in Equation 1. For example, from the slope of the logarithmic time (ln(t)) and temperature increase (T−T0), thermal conductivity λ is derived.

$$T - T_0 \cong \frac{q}{4\pi\lambda}[\ln(t) - \gamma - \ln(r^2/4\alpha)] \quad (1)$$

wherein
q=input power per length
γ=Euler constant
r=distance
α=thermal diffusivity The above methodology is applicable to in situ downhole measurement conditions. As depicted in FIG. 1, a dynamic system 10 according to one embodiment of the present invention includes a long and slender heater 12, such as a metal and/or plastic or other similar tube 20, and an array of temperature sensors 14, for example, a fiber optics sensor, located in a well 18 of a subsurface formation 16. The tube 20, such as a metal and/or plastic tube, may be deployed around the sensors 14 for protecting the sensors and for other purposes, such as distributed heating, as discussed in more detail below. Expected differences in temperature relaxation behaviors, i.e., thermal response, during heating and cooling, where the thermal properties of the formation differ, are shown graphically in FIG. 1. Herein, thermal conductivity measurements are used for purposes of describing the present invention. However, the present invention also contemplates other thermal property measurements, such as thermal diffusivity and thermal capacity.

Typically, borehole fluids would be directly surrounding the medium of the heater 20 and sensors 14 in a borehole. However, the present invention contemplates minimizing fluid convection effects as the first order of approximation.

In one embodiment of a system according to the present invention, an optical fiber sensor cable may be used as a distributed temperature sensing (DTS) system for the configuration depicted in FIG. 1. DTS systems are known in oilfield applications and will not be described in detail herein. Such DTS configurations provide consecutive temperature measurements along a well (note FIG. 1). Advantageously, the fiber sensor cable may be configured to provide temperature information and the metal and/or plastic or other similar tube of the cable may be configured as a heater by applying current to the tube.

Figure 2A:
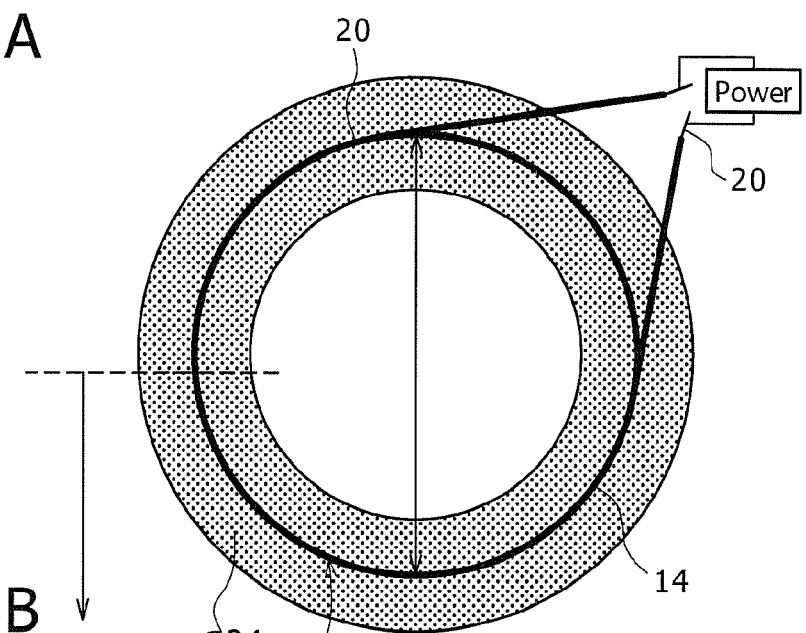
FIGS. 2A and 2B are schematic representations of a top view and a cross-sectional view, respectively, of a sensor cable-heater configuration used in an experimental system according to the present invention.
Figure 2B:
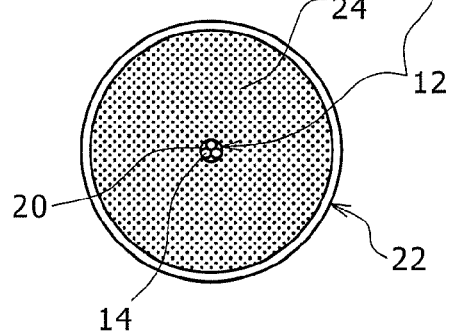

Applicants conducted experiments to evaluate the dynamic measurement methods and systems of the present invention. FIGS. 2A and 2B show top and cross-sectional views, respectively, of a sensor cable layout that was used in a modeling of the present invention. A cylinder shaped container 22 was filled with sand 24 with a sensor cable 12 positioned in the container 22 at the center and buried with the sand 24. Thermal conductivity of the sand was experimentally derived. The sensor cable 12 included a fiber sensor 14 and a steel tube 20 with a plastic sheath outside the tube. Input power for heating the tube 20 was applied at both ends of the tube 20, as depicted in FIG. 2A.

Thermal conductivity of the sand was measured in advance with commercially available equipment and was found to be 0.22 watts/meter/Kelvin [W/m/K].

Figure 3:
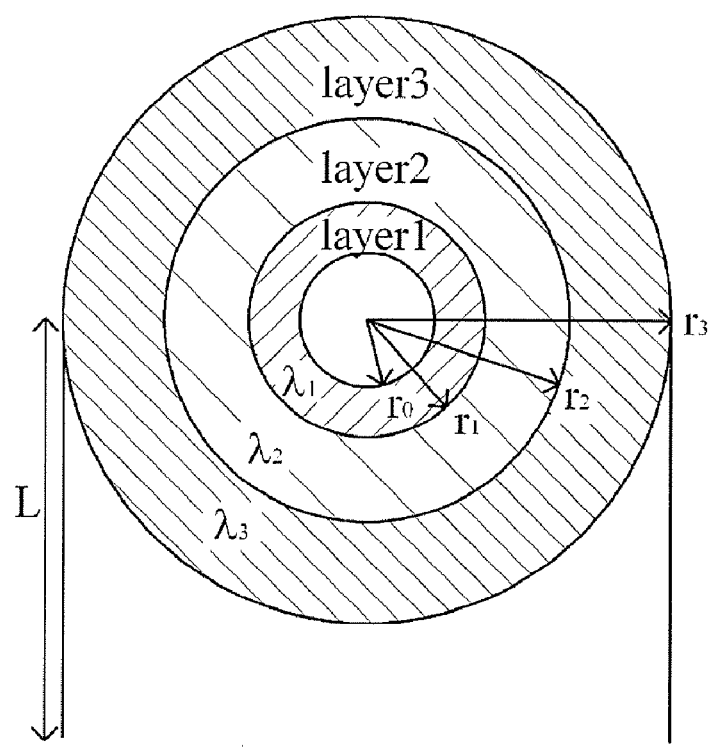
FIG. 3 is a schematic depiction of a model for the experimental configuration of FIGS. 2A and 2B in which layer 1 represents a sensor cable with plastic sheath configured as a heater; layer 2 represents sand; layer 3 represents air; and L represents cable length.
Figure 4:
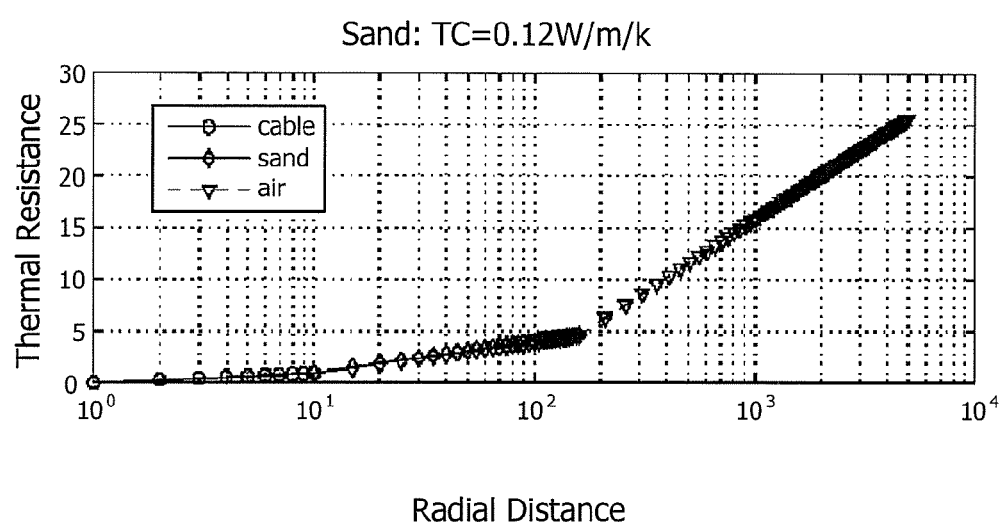
FIG. 4 is a graph of calculated thermal resistance versus radial distance for the model of FIG. 3.

FIG. 3 shows the experimental layout of FIGS. 2A and 2B in which homogeneous layers of cable with plastic sheath (layer 1), sand (layer 2), and air (layer 3) in the radial direction are assumed. FIG. 4 shows the calculated thermal resistance, expressed in Equation 2 below, plotted relative to the radial distance. It is assumed that the thermal resistance and the slope in Equation 1 (~1/λ) have a qualitatively similar tendency during a heat transfer process in time and radial distance.

$$\begin{aligned}R = &\ln\left(\frac{r}{r_0}\right)\bigg/(2\pi L \cdot \lambda_1), \, (r_0 < r \leq r_1) \quad (2)\\
= &\ln\left(\frac{r}{r_1}\right)\bigg/(2\pi L \cdot \lambda_2) + \ln\left(\frac{r_1}{r_0}\right)\bigg/(2\pi L \cdot \lambda_1), \, (r_1 < r \leq r_2)\\
= &\ln\left(\frac{r}{r_2}\right)\bigg/(2\pi L \cdot \lambda_3) + \ln\left(\frac{r_1}{r_0}\right)\bigg/(2\pi L \cdot \lambda_1) +\\
&\ln\left(\frac{r_2}{r_1}\right)\bigg/(2\pi L \cdot \lambda_2), \, (r_2 < r \leq r_3)\end{aligned}$$

Figure 5:
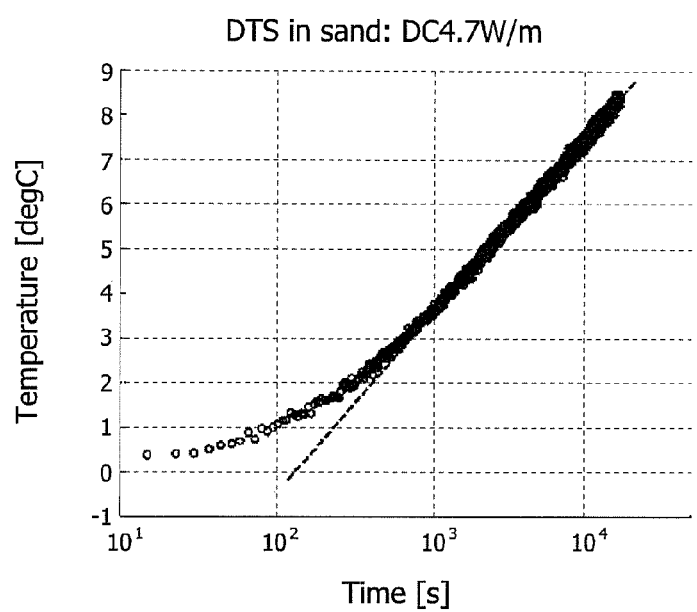
FIG. 5 is a graphical representation of temperature increase in sand while heating.
Figure 6:
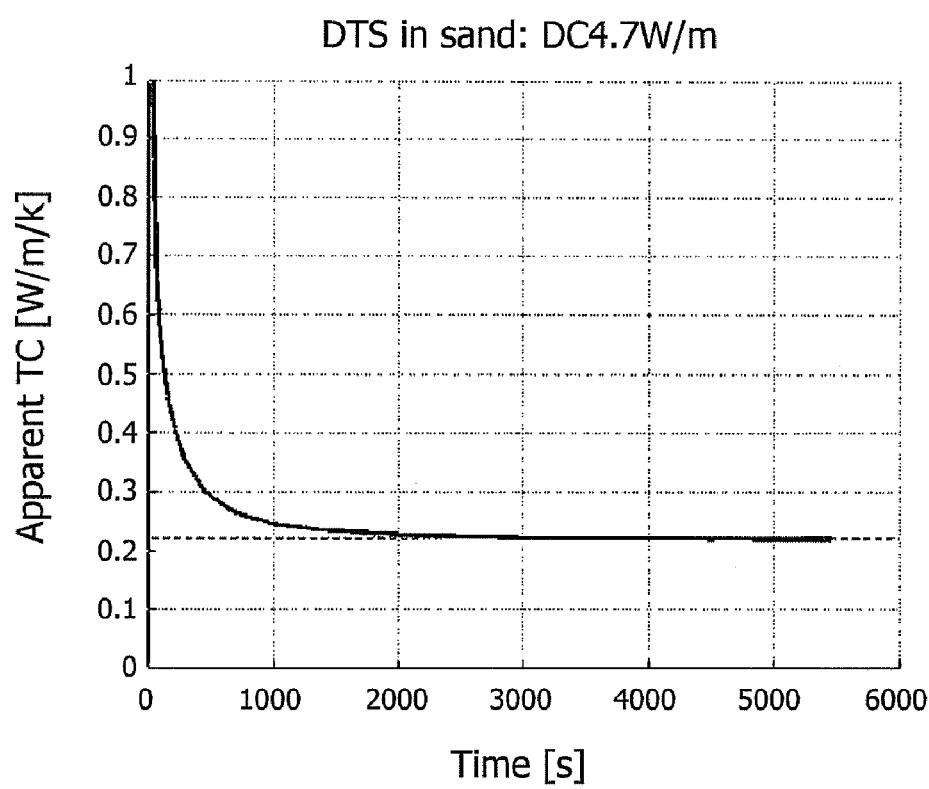
FIG. 6 graphically represents preliminary results of estimation of apparent thermal conductivity vs. time. Broken gray line indicates the estimated apparent thermal conductivity in sand.

FIG. 5 shows the measured temperature data during heating with 4.7 watts/meter [W/m]. The linear curve, as indicated by a broken black line, may be seen. This result versus time shows very similar response to the modeled thermal resistance curve versus radial distance in FIG. 4. The data were smoothed, i.e., polynomially fitted with moving windows, in time, then the derivative of dT/d(ln(t)) (the slope 1/4/pi/λ in Equation 1) was computed. The apparent thermal conductivity λ was obtained and plotted in FIG. 6. From the value of the almost flat part, as shown by the broken gray line in FIG. 6, the thermal conductivity was estimated as 0.22 W/m/K. The modeled result shows good correspondence with the pre-evaluated thermal conductivity in sand of 0.22 W/m/K.

Accordingly, through an experimental layout and modeling, applicants derived thermal conductivity in sand as a preliminary result, using methods and systems of the present invention.

Applicants further evaluated through numerical modeling applicability of a method of the present invention to in situ downhole conditions. A practical situation was assumed with a sensor cable supported by a pipe/casing put in a well (note FIG. 7). A plastic sheath covers the sensor cable. The measurement duration for necessary temperature increase, i.e., the temperature increase required for evaluating formation thermal properties, with a practical input power was evaluated. As discussed above, the predetermined period of time for active heating depends on several factors.

Figure 7:
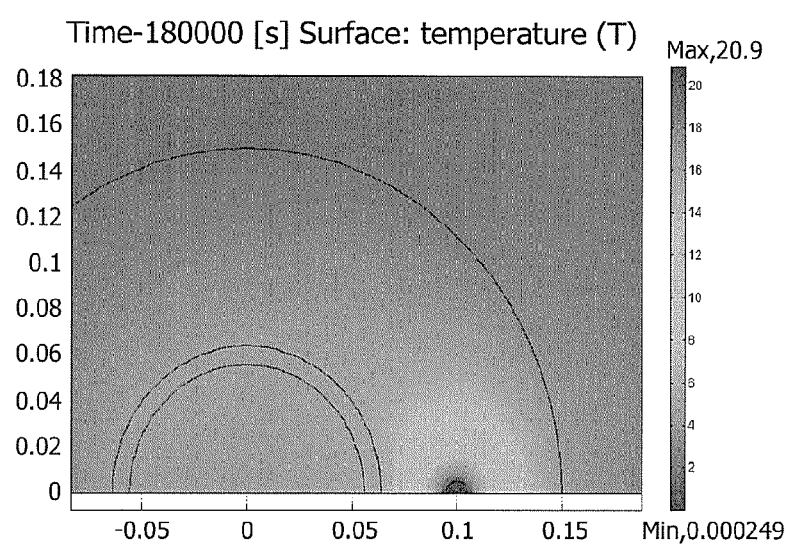
FIG. 7 is a computer simulation of heat transfer for a cross-section of a well. The sensor cable is located outside a casing that is a support pipe.
Figure 8:
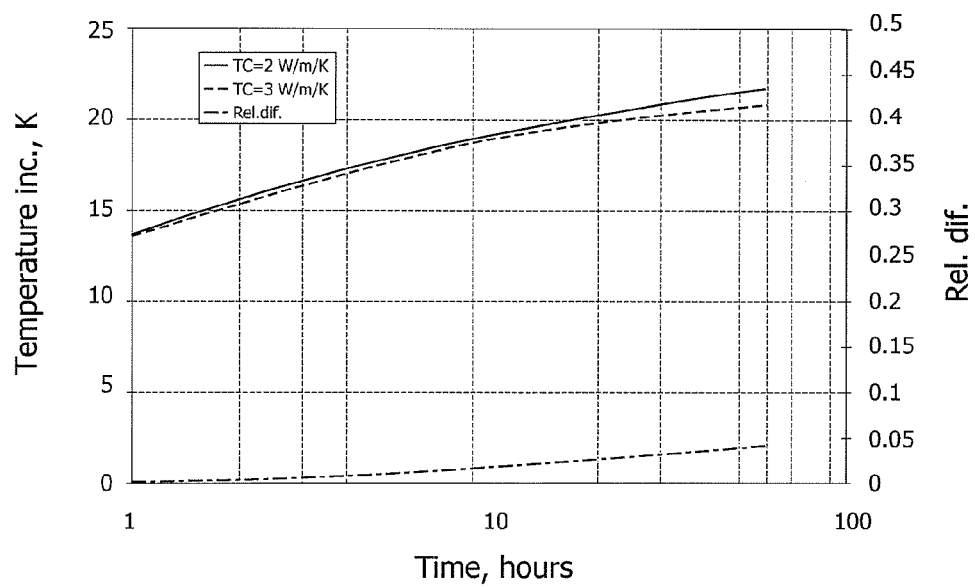
FIG. 8 is a graph representing influence of formation thermal conductivity ($\lambda f$) on temperature for a well diameter of 30 cm.
Figure 9:
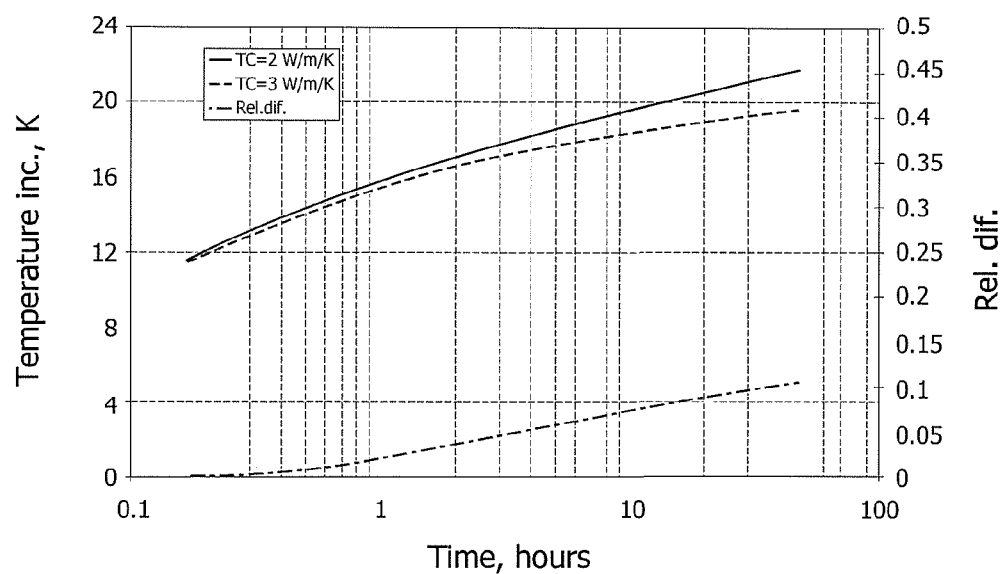
FIG. 9 is a graph representing influence of formation thermal conductivity ($\lambda f$) on temperature for a well diameter of 10 cm.
Figure 10:
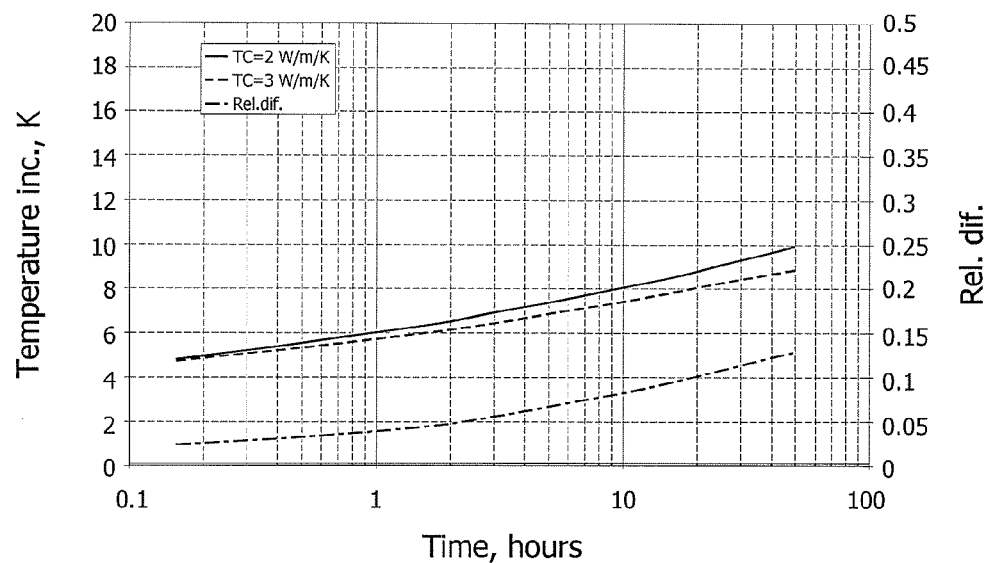
FIG. 10 is a graph showing influence of formation thermal conductivity ($\lambda f$) on temperature for a well with metal casing.
Figure 11:
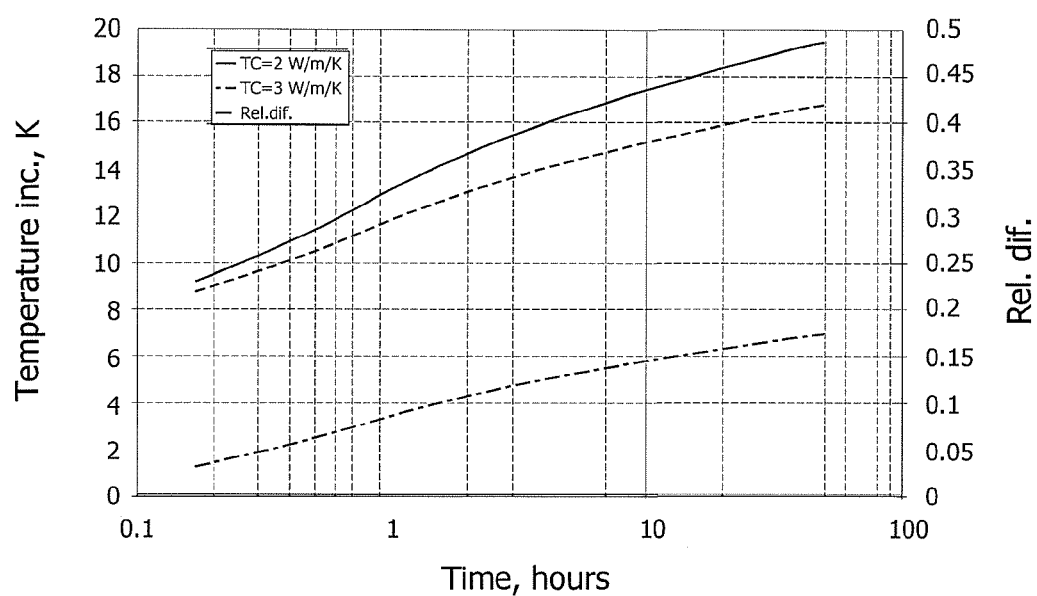
FIG. 11 is a graph showing influence of formation thermal conductivity ($\lambda f$) on temperature for a well with plastic casing.

Table 1 shows the parameters used in the numerical modeling. FIG. 7 shows a computer simulation of a temperature field for a cross section of the well with a heater sometime after heating. FIGS. 8 and 9 show graphically the temperature increase (ΔT) at the heater versus time during heating for well diameters of 30 cm and 10 cm, respectively. The pink lines in FIGS. 8 and 9 indicate when the formation thermal conductivity (λf) is 3 W/m/K, and the blue lines indicate conductivity of 2 W/m/K. The red lines show a relative increase of {ΔT (=3)−ΔT(λf=2)}/ΔT(λf=3). The result suggests that smaller well size may be preferred to differentiate temperature behavior between different thermal properties, since heat energy consumption relates to the volume of the fluid. However, even with a hole having a diameter of 10 cm, more than 2 days are required to achieve a 10% relative increase in temperature. To reduce the necessary measurement duration, FIGS. 10 and 11 show modeling focused on an effect of the material for the pipe. FIG. 10 is for a pipe made of metal and FIG. 11 is for a plastic pipe. In both cases, well diameter is 18 cm. A 10% relative increase in temperature is achieved in a few hours with the plastic pipe whereas the metal pipe required 20 hours. The plastic pipe works as a thermal isolator in the well to effectively transfer heat into the formation. By using a plastic pipe, the techniques of the present invention are enhanced for purposes of measuring temperature changes, and therefore thermal conductivity, in downhole environments.

The numerical modeling confirmed suitability of the present methodology to downhole applications, with some assumed conditions.

TABLE 1

Parameters for numerical modeling

|  | Thermal conductivity | Density [kg/m3] | Specific heat [J/kg*K] |
| --- | --- | --- | --- |
| Formation | 3 or 2 | 3000 or 2000 | 1000 |
| Fluid | 0.6 | 1000 | 4200 |
| Heater/sensor | 50 | 7800 | 500 |
| Pipe | 50 | 7800 | 500 |
| Plastic | 0.16 | 1300 | 1500 |
| Air | 0.024 | 1.25 | 1000 |
| Heater power |  | 30 W/m |  |

Applicants' experimental and modeling results confirmed applicability of in situ downhole thermal conductivity measurements according to the present invention. While evaluating factors such as fluid effect and appropriate cable and heater designs, preliminary experiments showed applicability of the present invention to measurements of thermal properties in surrounding media within an acceptable error range of around 10%.

In one embodiment of the present invention, a heating device may include a heater that utilizes an electrically insulated metal tube surrounding, for example, a fiber optics sensor, for generating heat in a subsurface structure by injecting current into the metal tube. In this, the metal tube may be sheathed with a suitable electrically insulating material, such as plastic and glass. For example, in situations where local heating of target depths in subsurface formations is preferred or desirable, current may be injected into an electrically insulated metal tube having higher resistivity at the target depths (note FIG. 12A). In this, a tube having appropriate resistivity as required by the localized heating may be utilized. Different resistivity in a tube may be achieved by using different materials for the tube. Alternatively, different heater density, for example, different numbers of winding around a fiber cable, may be utilized in combination with, or independently from, a heater tube having varying resistivity.

Figure 12A:
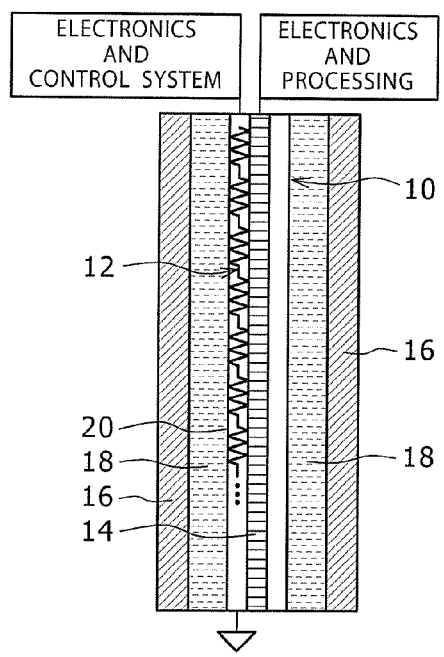
FIGS. 12A to 12D are schematic representations of exemplary systems for deriving thermal properties of subsurface structures according to the present invention.

FIGS. 12A to 12D are schematic depictions of some embodiments for dynamic measurements of thermal properties of subsurface formations according to the present invention. FIG. 12A depicts a system 10 having a distributed temperature sensing (DTS) system 12 with a fiber optics sensor 14 and a metal tube 20 deployed in a subsurface formation 16 having, for example, borehole fluid in a borehole 18. Since the fiber optics sensor 14 is in the thin metal tube 20, the metal tube 20 may be used as a heat generating or cooling device by, for example, sending a pulse-type or AC/DC current from the surface through the metal tube 20. Appropriate electronics and processing and control capability may be provided as schematically depicted in FIGS. 12A to 12D. In this, the configuration of FIG. 12A provides distributed temperature changes along a predetermined section of the well 18 and the formation structure 16.

The configuration of FIG. 12A has various benefits such as utilizing existing oilfield equipment that may be set up at a well site without need for additional equipment. The depicted configuration provides homogeneous and distributed heat generation and distributed temperature outputs in predetermined area or areas of interest for purposes of determining formation thermal properties thereof. However, in some situations, based on particular needs, the embodiment of FIG. 12A may cause heat leak or provide unnecessary heating in non-targeted zones of the subsurface formation. Moreover, acquired data may be an averaged response for a layered zone due to limitations in depth resolution or spatial sensitivity that are inherent in DTS hardware.

Figure 12B:
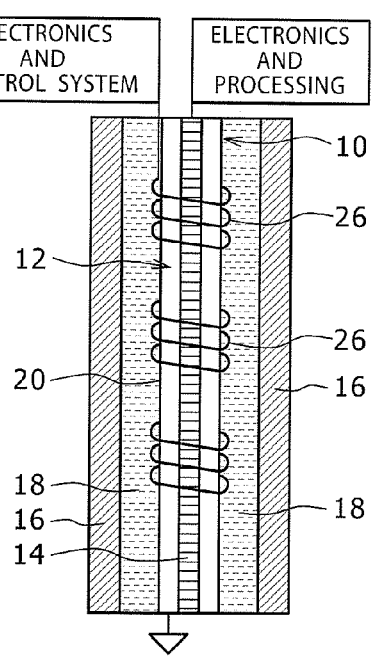

FIG. 12B provides one embodiment with a system 10 having a DTS system 12 with localized heaters 26 to heat selected, predetermined segments of the formation 16 having a well 18 therein. The embodiment of FIG. 12B having the DTS 12 with a localized heat generation device may be used in circumstances where the distributed heat generation configuration of FIG. 12A does not create adequate temperature disturbances in a well. Electrical current may be sent from the surface, or from a power device in the well 18. As in the embodiment of FIG. 12A, temperature along the well 18 may be monitored by the sensors 14. In the embodiment of FIG. 12B, the localized heaters 26 work efficiently in one or more target zones providing heat generation in the formation 16 as necessary or desirable. In this, more selective and targeted temperature variances may be generated. FIG. 12B depicts additional configuration that is required for the depicted embodiment, including a longer heater length that is sufficient to cover DTS spatial resolution.

Figure 12C:
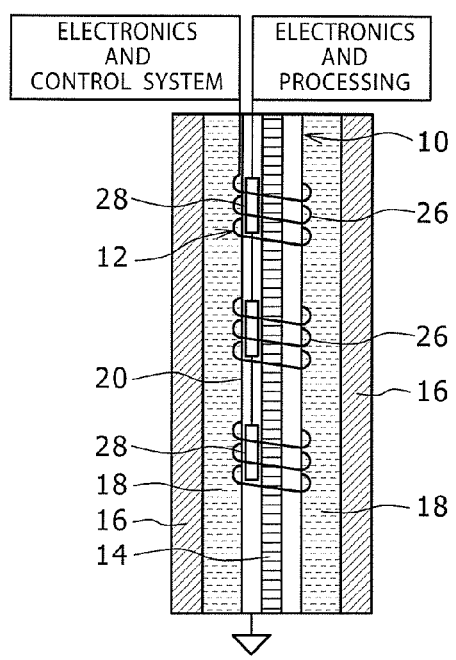

FIG. 12C depicts yet another embodiment of one system 10 having a DTS system 12 with localized heaters 26 and, in this embodiment, localized high precision temperature sensors 28. In the embodiment of FIG. 12C, the localized temperature sensors 28 may be used with a sensor cable 14 and localized heat generation devices 26, as discussed in other embodiments above. In this, in an instance where the DTS system 12 does not give a sufficiently high resolution in temperature and/or depth, the system 10 of FIG. 12C may be used with one or more localized heaters 26 in combination with one or more localized temperature sensors 28, such as Fiber Bragg Grating (FBG) sensors and resistor temperature detector (RTD) sensors, to provide suitable spatial and/or temperature resolution, as desirable or necessary. In the present embodiment, temperature variance may be monitored with the localized sensors 28 as well as the sensor cable 14.

Localized heaters, such as depicted in FIG. 12C, may be used to provide efficient, targeted heating in one or more predetermined zones of interest. In this, it is possible to acquire higher depth resolution by utilizing localized heaters and sensors, as depicted in the embodiment of FIG. 12C, although configuration in addition to the one depicted in FIG. 12A may be required to set up the system.

Figure 12D:
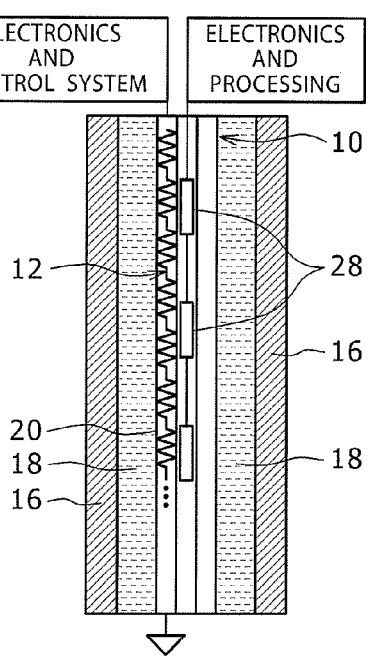

FIG. 12D depicts yet another embodiment of a system 10 for dynamic measurements of temperature having distributed metal and/or plastic or other similar tube heat generators 20, for example, with varying resistivity in one or more tubes, and localized high precision temperature sensors 28 deployed in a well 18 of a formation 16. In the embodiment of FIG. 12D, a distributed heater, such as an electrically insulated metal tube heat generator 20, may be used in configuration with localized high precision temperature sensors 28 in situations where a DTS system may not provide sufficiently high resolution in temperature and/or depth. In this, a heater 20 over the depth of the well 18 may be provided with localized temperature sensors 28, such as FBG and/or RTD sensors. Sensors (not shown), such as cable sensors in a DTS system, may be combined with the system 10 in FIG. 12D, if desirable or necessary.

In some embodiments of the present invention, dynamic temperature measurements may be acquired using an active heat generation device in a well, such as a hydrocarbon, carbon-di-oxide and/or water bearing well. The present invention contemplates applicability in methane hydrates and heavy oil bearing formations. As used herein, "heavy oil" refers to viscous oil deposits, such as heavy oil, tar sand, bitumen, oil sand, for which knowledge of thermal properties is desirable and/or necessary for purposes of development and extraction. For purposes of explanation, some embodiments of the instant invention are described herein with thermal disturbance/stimulation by a heat generation device; however, the present invention also contemplates utilizing a cooler, for example, a Peltier-type device, to disturb the temperature of a subsurface formation for purposes of thermal characterization of the formation. In this, the present invention contemplates wide applicability of the methods and systems disclosed herein to a range of endeavors that involve in situ characterization of thermal properties of subsurface structures for purposes of exploration and/or development of the structures.

The preceding description has been presented only to illustrate and describe the invention and some examples of its implementation. It is not intended to be exhaustive or to limit the invention to any precise form disclosed. Many modifications and variations are possible in light of the above teaching.

The preferred aspects were chosen and described in order to best explain principles of the invention and its practical applications. The preceding description is intended to enable others skilled in the art to best utilize the invention in various embodiments and aspects and with various modifications as are suited to the particular use contemplated. It is intended that the scope of the invention be defined by the following claims.

What is claimed is:

1. A system for deriving one or more thermal properties of a hydrocarbon-bearing formation for characterizing the formation comprising:
   a heating device configured for creating a thermal disturbance downhole in a predetermined area of interest; and
   a sensing system configured for acquiring thermal response data downhole for the thermal disturbance at two or more locations separated with respect to a length of a wellbore downhole and deriving at least one thermal property of the formation based on time variation in temperature of the area of interest, wherein the sensing system comprises two or more temperature sensors separated with respect to the length of a wellbore downhole and a processor configured for measuring temperature of the area of interest over a predetermined period of time, and the heating device includes a heater surrounding the two or more temperature sensors, for generating heat along the length of the wellbore penetrating the formation.

2. The system for deriving one or more thermal properties of a hydrocarbon-bearing formation according to claim 1, wherein the thermal property of the formation comprises one or more of thermal conductivity, thermal diffusitivity and thermal capacity of the formation.

3. The system for deriving one or more thermal properties of a hydrocarbon-bearing formation according to claim 1, wherein the heating device comprises at least one of a heater configured for active distributed heating of the predetermined area of interest and a heater configured for active local heating of the predetermined area of interest.

4. The system for deriving one or more thermal properties of a hydrocarbon-bearing formation according to claim 1, wherein the two of more temperature sensors are configured for downhole distributed sensing of temperature change.

5. The system for deriving one or more thermal properties of a hydrocarbon-bearing formation according to claim 1, wherein the two or more temperature sensors are configured for downhole localized sensing of temperature change.

6. The system for deriving one or more thermal properties of a hydrocarbon-bearing formation according to claim 1, wherein the sensing system comprises a sensor configured for downhole sensing of temperature change in the predetermined area of interest and the thermal response data comprises time variance of local temperature data.

7. The system for deriving one or more thermal properties of a hydrocarbon-bearing formation according to claim 6 further comprising a processor configured for determining thermal conductivity of the formation based on the time variance of local temperature data.

8. The system for deriving one or more thermal properties of a hydrocarbon-bearing formation according to claim 7, wherein the processor is configured for determining thermal conductivity of at least one of a methane hydrate and heavy oil bearing formation.

9. The system for deriving one or more thermal properties of a hydrocarbon-bearing formation according to claim 1, wherein the heating device and the sensing system comprise one or more of a distributed temperature sensing(DTS) system, a resistance heater, a Fiber Bragg Grating sensor or a resistor temperature detector(RTD).

10. The system for deriving one or more thermal properties of a hydrocarbon-bearing formation according to claim 9, wherein the resistance heater comprises one or more of a plastic tube or an electrically insulated metal tube.

11. The system for deriving one or more thermal properties of a hydrocarbon-bearing formation according to claim 9, wherein the heating device comprises an outer tube of the DST system.

12. The system for deriving one or more thermal properties of a hydrocarbon-bearing formation according to claim 1, wherein two or more sets of heating devices and sensing systems are provided at two or more locations separated with respect to a length of the wellbore downhole in which each of the two or more sets of heating devices and sensing systems are heated by their respective heating devices at substantially the same time.

13. A method of deriving one or more thermal properties of a hydrocarbon-bearing formation for characterizing the formation comprising:
   creating thermal disturbance downhole in a predetermined area of interest;
   acquiring thermal response data based on time variation in temperature of the area of
   deriving a thermal property of the formation based on the thermal response data of the formation, wherein acquiring thermal response data comprises measuring temperature of the area of interest at two or more locations separated with respect to a length of a wellbore downhole over a predetermined period of time and the thermal disturbance is created by a heating device including a heater element surrounding two or more temperature sensors separated with respect to the length downhole, for generating heat in the predetermined area of interest, wherein the heating device, including the heater and the two or more temperature sensors, is disposed along the length of the wellbore penetrating the formation.

14. The method of deriving one or more thermal properties of a hydrocarbon-bearing formation according to claim 13, wherein creating thermal disturbance downhole comprises active distributed heating of the area of interest.

15. The method of deriving one or more thermal properties of a hydrocarbon-bearing formation according to claim 13, wherein acquiring thermal response data comprises acquiring the data by situating two or more discrete temperature sensors downhole.

16. The method of deriving one or more thermal properties of a hydrocarbon-bearing formation according to claim 13, wherein acquiring thermal response data comprises acquiring the data by downhole distributed sensing of temperature change.

17. The method of deriving one or more thermal properties of a hydrocarbon-bearing formation according to claim 13, wherein acquiring thermal response data comprises acquiring the data by at least one downhole localized sensing of temperature change.

18. The method of deriving one or more thermal properties of a hydrocarbon-bearing formation according to claim 13, wherein acquiring thermal response data comprises downhole sensing of temperature change in the area of interest and the thermal response data comprise time variance of local temperature data.

19. The method of deriving one or more thermal properties of a hydrocarbon-bearing formation according to claim 18, wherein deriving a thermal property comprises providing the time variance of local temperature data to a processor for determining thermal conductivity of the formation.

20. The method of deriving one or more thermal properties of a hydrocarbon-bearing formation according to claim 13, wherein deriving a thermal property comprises determining one or more of thermal conductivity, thermal diffusivity or thermal capacity of the formation.

21. The method of deriving one or more thermal properties of a hydrocarbon-bearing formation according to claim 13 further comprising characterizing the formation by providing one or more answer products based on the thermal property of the formation, the answer products relating to nor or more of:
    characteristics of hydrocarbons in the formation for heat treatment of the hydrocarbons;
    one or more physical parameters of the formation for delineating the formation; or
    permanent monitoring of an operating well traversing the formation.

22. The method of deriving one or more thermal properties of a hydrocarbon-bearing formation according to claim 13 further comprising utilizing a hot wire method for deriving the thermal property of the formation based on the thermal response data of the formation.

23. The method of deriving one or more thermal properties of a hydrocarbon-bearing formation according to claim 22, wherein the thermal property comprises thermal conductivity of the formation.

24. The system for deriving one or more thermal properties of a hydrocarbon-bearing formation according to claim 13, wherein two or more sets of heating devices and sensing systems are provided at two or more locations separated with respect to a length of the wellbore downhole in which each of the two or more sets of heating devices and sensing systems are heated by their respective heating devices at substantially the same time.

25. A system for deriving one or more thermal properties of a hydrocarbon-bearing formation for characterizing the formation comprising:
    a heating device configured for creating a thermal disturbance downhole and provided across two or more locations separated with respect to a length of a wellbore interacting with the formation; and
    a sensing system configured for acquiring thermal response data downhole for the thermal disturbance at the two or more locations defined by the heating device and deriving at least one thermal property of the formation based on time variation in temperature,
    wherein the sensing system comprises two or more temperature sensors located downhole at the two or more locations defined by the heating device and a processor configured for measuring temperature at the two or more locations over a predetermined period of time, and the heating device includes a heater that utilizes an electrically conductive element surrounding the two or more temperature sensors, for generating heat by injecting current into the electrically conductive element,
    wherein the heating device and the sensing system comprise one or more of a distributed temperature sensing (DTS) system, a resistance heater, a Fiber Bragg Grating sensor or a resistor temperature detector (RTD), and wherein the resistance heater comprises a tube with varying resistance configured for downhole localized heating of the formation.

* * * * *